(12) United States Patent
Thevenin et al.

(10) Patent No.: US 6,295,337 B1
(45) Date of Patent: Sep. 25, 2001

(54) DIGITAL RADIOGRAPHY DEVICE PROTECTED AGAINST RISK OF ELECTROCUTION

(75) Inventors: Bernard Thevenin, St Egreve; Francis Glasser, Eybens, both of (FR)

(73) Assignee: Commissariat A l'Energie Atomique, Paris (FR)

( * ) Notice: Subject to any disclaimer, the term of this patent is extended or adjusted under 35 U.S.C. 154(b) by 0 days.

(21) Appl. No.: 09/403,957
(22) PCT Filed: May 15, 1998
(86) PCT No.: PCT/FR98/00977
§ 371 Date: Nov. 19, 1999
§ 102(e) Date: Nov. 17, 1999
(87) PCT Pub. No.: WO98/53340
PCT Pub. Date: Nov. 26, 1998

(30) Foreign Application Priority Data

May 16, 1997 (FR) .................................................. 97 06049

(51) Int. Cl.⁷ ..................................................... H05G 1/54
(52) U.S. Cl. ........................... 378/117; 378/98.8; 378/189
(58) Field of Search .................................... 378/98.8, 117, 378/189

(56) References Cited

U.S. PATENT DOCUMENTS 5,434,418    7/1995   Schick .
5,454,022  * 9/1995   Lee et al. .............................. 378/98.8
5,912,942  * 6/1999   Schick et al. ........................ 378/98.8
6,044,131  * 3/2000   McEvoy et al. ...................... 378/162

FOREIGN PATENT DOCUMENTS 0 544 974 A1   11/1991   (EP) .
0 666 483 A2   1/1995    (EP) .

* cited by examiner

Primary Examiner—Robert H. Kim
Assistant Examiner—Hoon Koo Song
(74) Attorney, Agent, or Firm—Pearne & Gordon LLP

(57) ABSTRACT

The present invention relates to a digital radiography device with protection against electrical risks, having:

a radiation source (10);

a sensor (12) connected to an electronic card (13) of a computer (14), first and second assemblies (20, 21) isolated from each other from the galvanic point of view, the first assembly (20) comprising electronic means connected to the sensor (12), the second assembly (21) comprising means for supplying a voltage for supplying the sensor (12) during the presence of radiation and a voltage for supplying the sensor part of the card (13), and means for providing management of the sensor, recovery of the data and processing thereof; the two assemblies (20, 21) exchanging information by optical means.

10 Claims, 3 Drawing Sheets

DIGITAL RADIOGRAPHY DEVICE PROTECTED AGAINST RISK OF ELECTROCUTION

DESCRIPTION

1. Technical field

The present invention relates to a digital radiography device with protection against electrical risks.

This device can advantageously be used in the field of digital dental radiography.

2. Prior art

The present invention is situated in the medical field and relates to any device which combines a diagnostic or treatment device with an acquisition, control and/or treatment system, using the mains for its electrical supply or supplies of another type whose voltage exceeds safety low voltages.

Such a connection of one of the elements of the equipment to the mains must cause no risk to the patient, operator and/or third parties. Various standards oblige the manufacturer to review all the risks which may be presented by his equipment vis-à-vis such people and to afford a remedy for them preventatively, as from the design and manufacture, by taking appropriate steps of such a nature as to mitigate the risks identified.

The digital medical radiography devices which currently exist on the market take into account the electrical risks in a conventional fashion. Usually, a "relay box" is placed on the sensor/computer path, whose essential function is to establish an isolation barrier on the sensor/computer path, as well as vis-à-vis the mains supplying the energy. This relay box has a double-insulation mains supply, which satisfies current standards, and supplies power to local electronics and to the remote sensor. These local electronics transform the analogue signal coming from the sensor into digital signals, so that any exchange with the computer relates only to the digital signals passing through optical couplings (optocouplers) isolating the sensor from the computer on an electrical level. Thus the sensor is isolated from the mains at the relay box by a supply including a double-insulated transformer and, at the computer, by the presence of an optical barrier on the data path.

Such a technique significantly increases the cost incurred for protection against electrical risks and introduces a second risk element, namely an independent power supply, without eliminating the computer, from which it is also necessary to be protected.

The object of the invention is a device for guarding against any electrical risks which may be feared, when one of the elements constituting it is supplied with power from the mains, or any other source if voltages are higher than safety low voltage.

SUMMARY OF THE INVENTION

The invention proposes a digital radiography device with protection against electrical risks, having:

a radiation source, for example X-rays;

a sensor connected to an electronic card of a computer, characterised in that it comprises first and second assemblies isolated from each other from the galvanic point of view, the first assembly comprising electronic means connected to the sensor, the second assembly comprising means for supplying a voltage for supplying the sensor during the presence of radiation and a voltage for supplying the sensor part of the card, and means for providing management of the sensor, recovery of the data and processing thereof, the two assemblies exchanging information by optical means, and in that the two assemblies cohabit within the electronic card.

Advantageously, the two assemblies are surrounded by a belt of air.

Advantageously, the first assembly comprises electronics located on the electronic card and disposed in a galvanic isolation enclosure situated on the said card, the sensor and a connecting cable connecting the sensor and the said electronics.

Advantageously, the electronics of the sensor assembly are protected by an isolating belt, the connection between isolating enclosure and connecting cable being effected by a movable plug passing through the metallic enclosure of the computer, this plug having insulation reinforced by superimposed moulding, the fixed base of the connector which receives the plug being situated recessed in the isolation enclosure. The analogue data issuing from the sensor are digitised in the sensor electronics within the isolation enclosure.

Advantageously, the power necessary to the isolation assembly is taken off in the computer assembly downstream from the safety power supply, on low voltage supplies, and transmitted by means of DC/DC converters situated on the electronic card.

The device of the invention can notably be used in the field of dental radiography.

The device of the invention protects the patient and operator against potential but uncertain electrical risks. This device provides an isolation barrier ensuring compliance with electrical standards between a sensor, or any other element, in contact with a patient at one end and, at the other end, control and/or processing electronics, supplied with power from the mains.

The device of the invention is advantageous because of its simplicity, and therefore its cost, since it uses electrical protection, processing of the data issuing from a sensor within a single electronic card and display of these data without sacrificing any of the elementary requirements of diagnostic equipment.

The invention can be applied to any passive or active sensor in contact with a patient so long as:

it receives, for its functioning, energy, possibly electrical stimuli, coming from equipment connected to the mains, or provided with a self-contained power supply, so long as its voltage exceeds the safety low voltage level (50 volts);

it supplies, possibly, in return, measuring signals or parameters, so long as these signals are sent to processing electronics supplied from voltage sources whose voltage exceeds safety low voltages, all the more so when it is a case of the 220 volts 50 or 60 Hz mains.

DETAILED DISCLOSURE OF ONE EMBODIMENT

Figure 1:
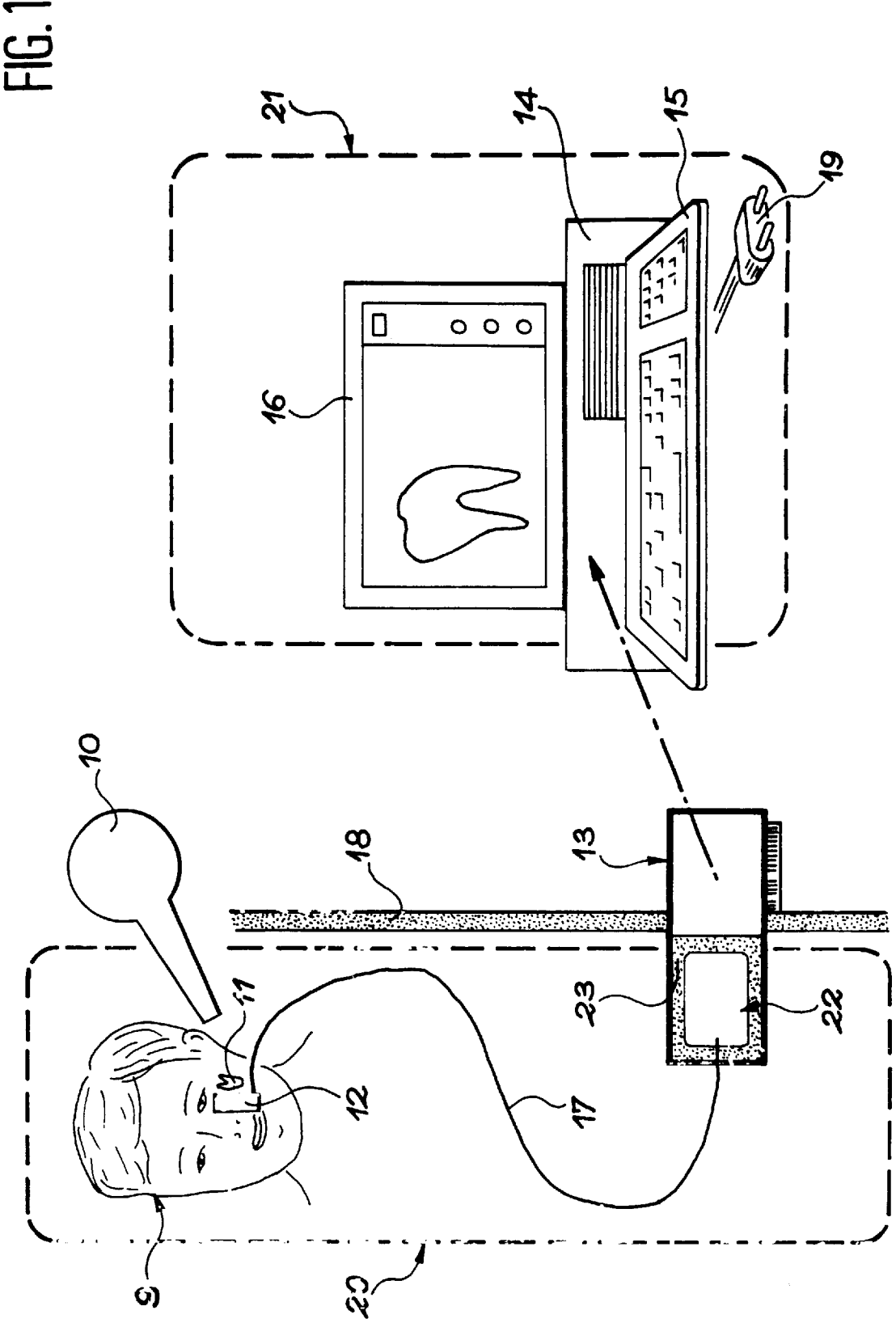
FIG. 1 illustrates the elements making up the device of the invention.

As illustrated in FIG. 1, the digital radiography device according to the invention comprises the elements making up a conventional digital radiography device, namely:

a radiation source 10 which emits radiation in the direction of the object 11 to be analysed, where this radiation can be X-rays or gamma radiation;

at least one image sensor 12 placed behind the object 11, with respect to the radiation source 10, this sensor 12 ensuring the transformation of the radiation received from the source 10 into information relating to the transparency of the object 11 to radiation;

a device for processing this information.

The object 11 considered, by way of example, in FIG. 1 is the tooth of a patient 9, of which it is wished to take a radiograph.

The processing device, depicted in this Figure, is a dedicated electronic card 13 of a computer 14, for example of the personal computer type, with its normal environment, notably a keyboard 15 and a display screen 16. This card 13, depicted outside the computer 14 in this figure, is in reality inside, in a standard location provided for this purpose. It is connected to the sensor 12 by means of a connecting cable 17.

This card 13 provides simultaneously:

management of the sensor 12 under the control of the computer 14;

recovery of the measuring data in the sensor 12 for the purpose of examination;

the digitisation of these data, and then their transfer to the computer 14, which processes them and presents, on the display screen 16, the radiographic image of the object 11 under consideration.

The sensor 12, which is here a digital dental radiography sensor, is associated with an X-ray generator 10, but has no physical or electrical link with it. It replaces the radiographic film normally used, which it was necessary to develop. This pixellated active intra-oral sensor forms, when it receives X-rays, a radiographic image, translated into electrical charges at each pixel, which is displayed on the screen of the computer 14, approximately one second after the end of emission of the X-rays.

Figure 2A:
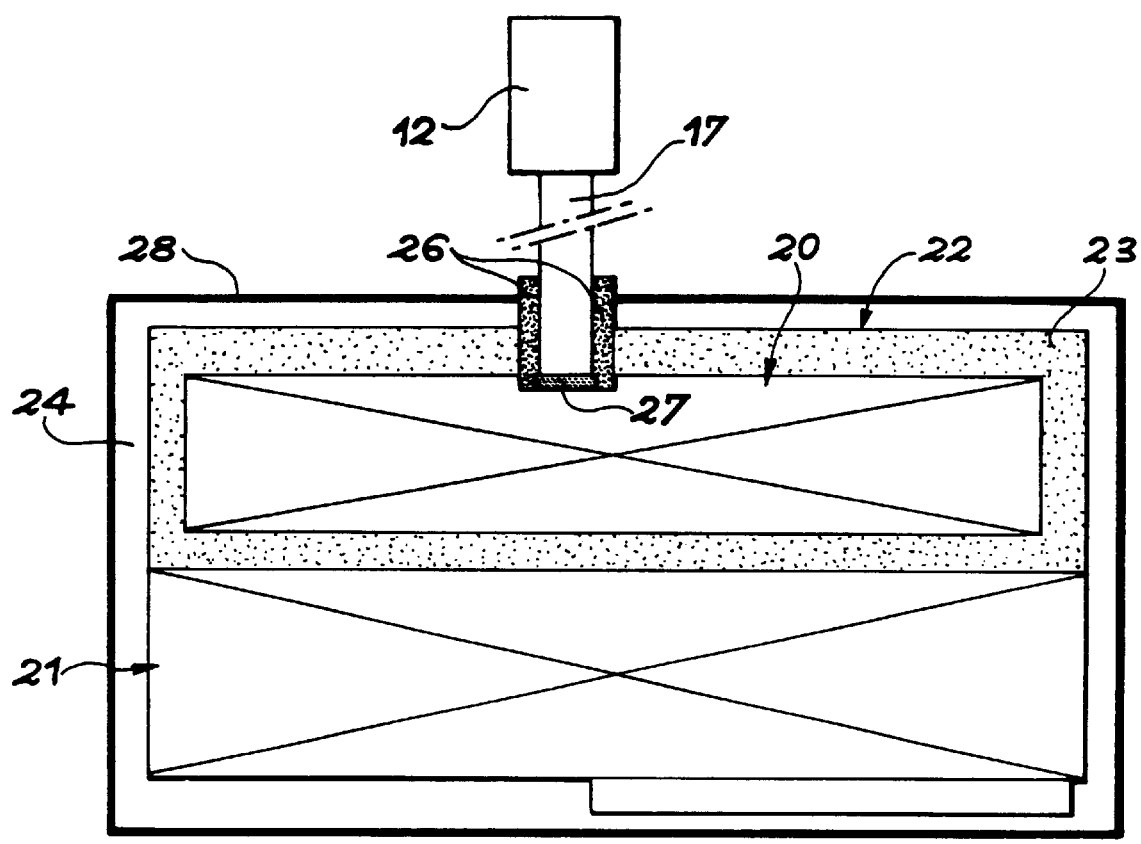
FIGS. 2A and 2B illustrate the device of the invention, showing its important characteristics with regard to isolation, FIG. 2B being a plan view.

According to the invention, as depicted in FIGS. 1 and 2A, the electronic card 13 is divided into two assemblies: a sensor assembly 20 and a computer assembly 21, which are isolated galvanically and can withstand a test voltage in accordance with the standards.

FIG. 1 depicts symbolically an isolation barrier 18 between these two assemblies.

The sensor assembly 20 comprises on the one hand electronics placed in a galvanic isolation enclosure 22 and on the other hand the connecting cable 17 which connects the sensor proper 12 to this isolating enclosure.

The electronics of the sensor assembly 20 are protected by an insulant (epoxy 23 or air 24) for the computer assembly 21, deemed to be at risk merely because it draws its power 19 from the mains. This protection consists at a minimum of an epoxy insulating belt 23 with no conductor on its surface, or in its thickness. This insulating belt partly juxtaposes the electronic assembly of the computer, and allows protected exchanges between the two assemblies 20 and 21. This insulating belt 23, reinforced by layers of air 24, also provides isolation vis-à-vis the metallic enclosure 28 of the computer.

The connection between isolating enclosure 22 and sensor 12 is effected by a movable plug 25 passing through the casing 28 of the computer 14 with, at right angles with the area passed through, reinforced insulation 26 withstanding for example 4,000 volts.

This passing through of the casing 28 by the movable plug 25 complies with specific positioning, shape and isolation provisions, namely:

The fixed base 27 of the connector which receives the plug 25 is situated inside the isolating enclosure 22. The connection boundary of the movable part on the fixed part (base 27) is effected in the isolating enclosure 22 recessed by at least 8 mm from the risk area. This imposes no particular constraint for the connector used and does not limit the choice thereof.

The movable plug 25 has a special moulding, which constitutes, vis-à-vis the cable 17, an increased isolation at right angle with the risk area represented by the passing through of the enclosure. This moulding carries a locating element, and a shape assisting gripping and removal.

The provisions adopted allow the use of a connector (plug and base) which does not have any particular voltage withstand strength (500 volts suffice).

The analogue data coming from the sensor 12 (two parameters: dose and video) are digitised in the sensor assembly 20, inside the isolating enclosure 22, so as to pass in digital form into the computer assembly, which simplifies this passage. The data exchanged bidirectionally between the two assemblies 20 and 21 are of the digital type and pass for example through optocouplers OPCa, OPCb and OPCc from the computer assembly 21 to the sensor assembly 20 and vice versa, which affords galvanic isolation. These optocouplers are not bidirectional: some provide a passage of the signals from the computer assembly to the sensor; the others do the opposite.

The power necessary to the sensor assembly 20 is taken off in the computer assembly 21 downstream from the safety supply (double-insulation supply imposed by the standards), at low voltage supplies (+5V and +12V), and transmitted in the safety enclosure (sensor assembly 20) by DC/DC converters (DC=direct current) with high insulating power (4,000 volts typical).

This design results in putting in series, vis-à-vis the mains, the insulation proper of the computer supply (already reinforced at 3,750 volts) and the insulation of the power and signal transfer devices (DC/DC converters and optocouplers).

The concept of "assembly" is introduced in order to describe the reality of total galvanic isolation between two physical regions of the same card. These two electrical assemblies cohabit within the card 13, but under no circumstances allow the passage of an electric current from one assembly to the other. On the electrical level, the two assemblies 20 and 21 ignore each other completely.

Figure 2B:
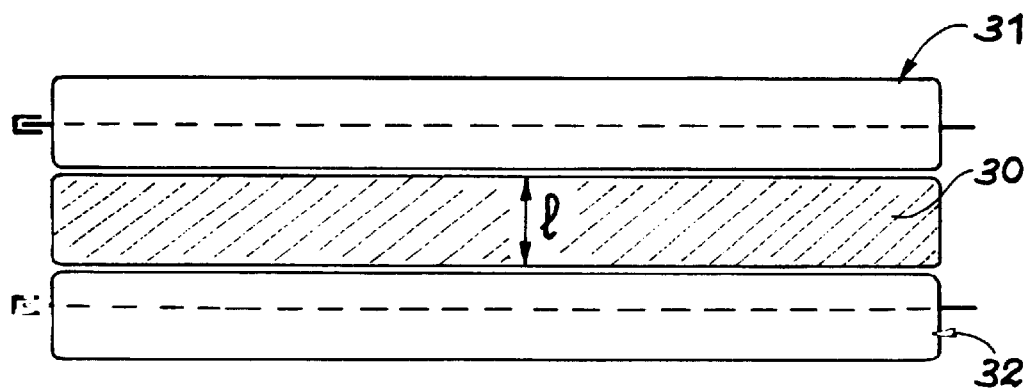

As illustrated in FIG. 2B, by means of the spacing 1 between two cards 31 and 32, it is a protected volume which is included in the computer assembly (layer of air 30 between two adjacent cards, one of them possibly being the card 13).

The sensor assembly 20 therefore comprises:

the electronics located on the card 13 in the isolating enclosure 23;

the single-piece assembly consisting of connector 25, cable 17 and sensor 12. The connector 25 enables this sensor electronics to be connected with the application (the patient), via the cable 17 (for example four metres long).

The computer assembly comprises:

a metallic casing 28;

a bus by means of which the processor exerts its control over the device, and sends or receives data;

electronics located on the card 13 in direct connection with the bus (ISA bus) supplied by the +5V and +12V supplies of the computer.

Everything which isolates the computer assembly 21 from the sensor assembly 20 is designed to be subjected to a test voltage of 4,000 volts. On the other hand, the assembly consisting of connecting cable 17 and sensor 12, which has no voltage greater than 50 volts DC, is subject to a reduced isolation requirement at 500 volts.

The isolation of the enclosure 22 vis-à-vis the computer electronics 21 is ensured at a minimum by the epoxy 23 of the printed circuit with no conductor in an area of approximately 8 mm.

The isolation of this same enclosure 22 vis-à-vis the casing 28 of the computer includes the same epoxy insulation, with in addition a layer of air of several millimetres, or even several centimetres.

The isolation of the enclosure 22 on the card 13 vis-à-vis adjacent cards is provided by a layer of air 30 guaranteed by the separation between the connectors of these cards, which is around 20 mm (necessary regulatory separation 4 mm). This is therefore in reality a volume which is protected.

Figure 3:
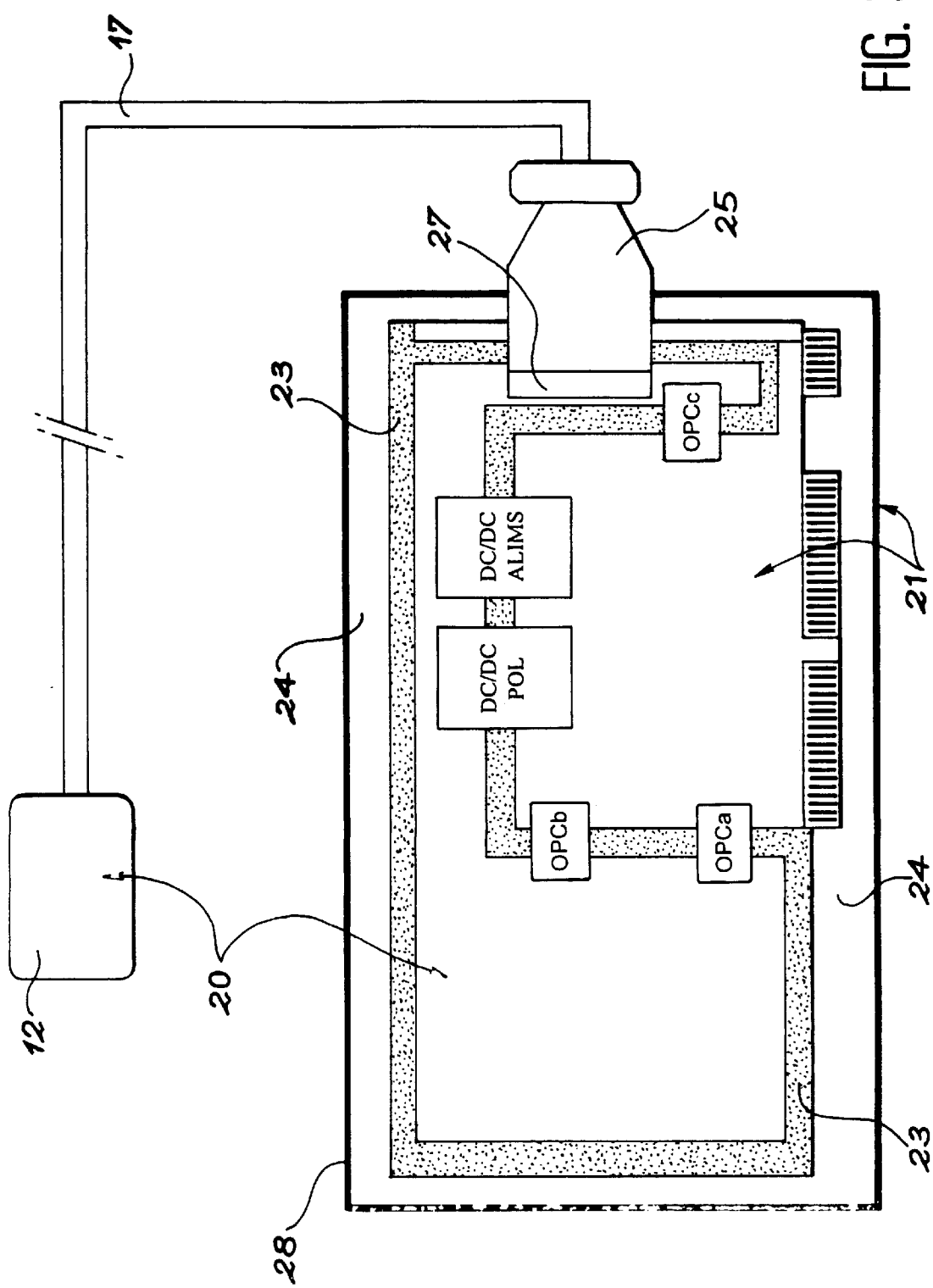
FIG. 3 illustrates more precisely the arrangement of the electronic card of the device of the invention.

The DC/DC converters (DC/DC POL and DC/DC ALIMS), illustrated in FIG. 3, fulfill a dual task:

The passage of power from one assembly to the other takes place with galvanic isolation. The electrical power becomes magnetic by virtue of a transformer primary, and then magnetic becomes electrical again on one or more secondary windings, which are isolated according to specific constraints.

The power taken off in an assembly can be rendered on one or more voltage sources, usually having different values from the input values.

For the converter DC/DC ALIMS, there are two voltage sources as an output: +5V and −5V.

The converter DC/DC POL obeys another law: its output voltage is ten times the input voltage (range 2 to 12 volts at the input giving 20 to 120 volts as an output). It is also provided with logic control enabling it to be started up during the operating time strictly necessary, i.e. in the presence of X-rays (typically 0.1 seconds).

The two elements described above are defined by the isolation voltage withstood between the input source and the output source or sources, for example 4,000 volts.

If the standards change, the specification of these elements changes, the isolation principles used in the device of the invention remaining valid. Implementation of the invention as defined above is made possible by virtue of the following elements:

All the surface area requirements of the electronics belonging to the sensor assembly 20, and the surface area requirements of the computer electronics 14, are drastically reduced through the use of highly integrated elements, so that these two assemblies 20 and 21, being satisfied with very much reduced surface areas, can be implanted without difficulty on an electronic card.

The possibility of dealing with electronic problems and at the same time the problems related to safety on an electronic card 13 similar in appearance to any other one, by means of simple arrangements, constitutes an important economic advantage.

The safety isolating enclosure 22 of the sensor assembly 20 has a common boundary with the computer assembly 21 deemed to be hostile but it could have opposite a second hostile world, consisting of a few signals coming from the X-ray source for example. In this case, the principles set out remain the same, the sensor assembly 20, in its enclosure 22, protecting itself from two or N assemblies deemed to be hostile.

The measurements made for the sensor assembly 20 to leave the computer assembly 21 are also very specific in that:

The fixed base 27 of the connector 25 and the connection/disconnection plane are situated in the isolating enclosure 22, recessed from the front face of the card (computer assembly) and the mechanical cover of the computer (recessed by a minimum of 8 mm).

The movable plug 25 connecting the cable 17 and sensor 12 to the card 13, once in place, passes through the front face of the card 13 and the casing 28, with, at right angle with this passing, a reinforced isolation, in accordance with the standards.

These provisions would be valid for any casing other than that of a computer. The result of this provision is that the above isolation constraints in no way relate to the connector proper, which can have a conventional isolation of 500 volts, which opens many possibilities of choice, whilst limiting the cost.

No reliance is placed on the relative shape of each assembly implanted on the card 13, nor the proportions of each of the surfaces. The boundary may, by means of appropriate contours, be elongated or reduced according to the requirements of exchange between the assemblies. This boundary can be established between signals coming from the computer and if applicable signals coming from outside.

The principle of the invention remains valid for higher isolation voltages by enlarging the epoxy barrier to a value commensurate with the requirement, and using DC/DC converters and optocouplers complying with the new requirement.

The principle of the invention remains valid for any electronic card belonging to other systems (mechanical and electrical through their buses: VME, VXI, PCI, PCMCIA bus) present and future, so long as they have a potential electrical risk for a patient or operator.

The sensor in contact with the patient can be of any other nature, passive or active, provided that there exists a need to protect against electrical risks.

Not having recourse to a relay box, placed on the cable and responsible for dealing with isolation problems, has another decisive advantage: taking the power supplies of the computer 14 as the power source for supplying the sensor assembly 20, through the high-isolation DC/DC converters, a chain of protections in series is formed. This is because the current standards impose on the computer power supply an isolation of 3,750 volts and a device having an increased isolation or double insulation. Starting from these voltage levels already protected and adding an additional protection barrier, the final level of protection is doubled.

What is claimed is:

1. A digital radiography device with protection against electrical risks, having:

a radiation source;

a sensor connected to an electronic card of a computer;

two assemblies isolated from each other from the galvanic point of view: the first assembly comprising electronic means connected to the sensor and the second assembly comprising means for supplying a voltage for supplying the sensor during the presence of radiation and a voltage for supplying the sensor part of the card, means for providing management of the sensor, recovery of the data issuing from the latter and processing thereof; the two assemblies exchanging information by optical means, the two assemblies cohabiting within the electronic card.

2. A device according to claim 1, wherein the radiation source is an X-ray source.

3. A device according claim 1, wherein the two assemblies on the electronic card are surrounded by a belt of air.

4. A device according to claim 1, wherein the first assembly comprises electronics located on the electronic card and disposed in a galvanic isolation enclosure situated on said electronic card, the sensor, and a connecting cable connecting the sensor to these electronics.

5. A device according to claim 4, wherein the electronics of the sensor assembly are protected by an isolating belt.

6. A device according to claim 4, wherein the connection between isolating enclosure and connecting cable is effected by a movable plug passing through the metallic casing of the computer, this plug having insulation increased by superimposed moulding.

7. A device according to claim 6, wherein the fixed base of the connector, which receives the plug, is situated recessed in the isolating enclosure.

8. A device according to claim 4, wherein the analogue data issuing from the sensor are digitized in the sensor electronics within the isolating enclosure.

9. A device according to claim 1, wherein the power necessary for the sensor assembly is taken off in the computer assembly downstream from the safety supply, on the low-voltage supplies, and transmitted by means of DC/DC converters situated on the electronic card.

10. Use of the device according to any one of the preceding claims, in the field of dental radiography.

* * * * *